United States Patent [19]

Masuda

[11] Patent Number: 4,812,475
[45] Date of Patent: Mar. 14, 1989

[54] NEW METHOD OF TREATMENT USING PROSTAGLANDIN ANALOGUES

[75] Inventor: Yoshinobu Masuda, Osaka, Japan

[73] Assignee: Ono Pharmaceutical Co., Ltd., Osaka, Japan

[21] Appl. No.: 935,153

[22] Filed: Nov. 25, 1986

Related U.S. Application Data

[63] Continuation of Ser. No. 757,476, Jul. 22, 1985, abandoned.

[30] Foreign Application Priority Data

Jul. 23, 1984 [JP] Japan ................... 59-152718

[51] Int. Cl.$^4$ ............................................. A61K 31/40
[52] U.S. Cl. ................................................ 514/412
[58] Field of Search .................................. 514/412

[56] References Cited

U.S. PATENT DOCUMENTS

| | | | |
|---|---|---|---|
| 4,234,597 | 11/1980 | Hayashi et al. | 514/412 |
| 4,313,954 | 2/1982 | Wakatsuka et al. | 514/412 |
| 4,315,013 | 2/1982 | Skuballa et al. | 514/412 |
| 4,499,085 | 2/1985 | Masuda | 514/690 |

FOREIGN PATENT DOCUMENTS 0015227  9/1980  European Pat. Off. ............ 514/412

Primary Examiner—Stanley J. Friedman
Attorney, Agent, or Firm—Stevens, Davis, Miller & Mosher

[57] ABSTRACT

The invention relates to a new method for the treatment of anoxia of brain cells using a $PGI_1$ derivative of the formula:

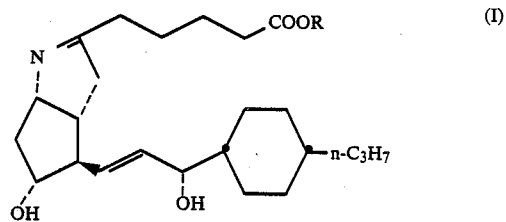

(wherein R represents an alkyl group of 1 to 4 carbon atoms.) or cyclodextrin clathrates thereof, or non-toxic salts thereof.

4 Claims, No Drawings

NEW METHOD OF TREATMENT USING PROSTAGLANDIN ANALOGUES

This application is a continuation, of application Ser. No. 747,476, filed 7/22/85, now abandoned.

The present invention relates to the prevention or treatment of anoxia of brain cells using a cis-16,19-ethano-ω-dihomo-6,9α-nitrilo-PGI₁ alkyl ester of the general formula (I):

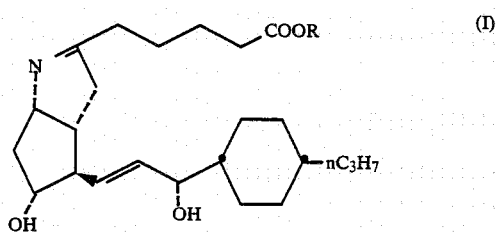

(wherein R represents an alkyl group, containing from 1 to 4 carbon atoms in a straight- or branched-chain or cyclodextrin clathrates thereof, or non-toxic salts thereof.

The brain is one of the most active organs in energy metabolism. When the homeostatic mechanism of the brain fails due to physical compression, brain cells are exposed to a state in which oxygen is deficient and the brain cannot function normally. The state in which brain cells are deficient in oxygen (hereinafter referred to as brain anoxia) causes cerebral edema and the accentuation of brain pressure which results from this vicious circle causes further oxygen deficiency and the disturbance becomes serious.

At present, hypnonarcotic agents, such as phenobarbital and thiobarbital, are employed to treat anoxic diseases of brain cells, but the dose of these agents which is sufficient to produce their desired effect affects the entire central nervous system. As a result, they exert an adverse influence on respiratory organs and circulatory organs, in the prevention of respiration or in their effect on the blood pressure-controlling center.

Accordingly, it has been strongly desired to develop compounds useful for the prevention or treatment of anoxia of brain cells but free from the side effects caused by hypnocarcotic agents and exhibiting their therapeutic effects at a low dose.

Up to this time, various PGI₁ and PGI₂ analogues have been synthesized and their pharmacolotical activities appraised. 16,19-ethano-ω-dihomo-6,9α-nitrilo-PGI₁ methyl ester is described in Example 2(4) of U.S. Pat. No. 4,234,597. The protective effect against brain anoxia of various PGI₁ and PGI₂ analogues is described in Japanese Patent Publication No. Showa 58-192821 and West German Patent Publication No. 3,315,356, and specifically the protective effect against brain anoxia of 16,19-ethano-ω-dihomo-6,9α-nitrilo-PGI₁ methyl ester is described in an Experimental Example.

However, in the above-mentioned patent publications there is no description concerning stereoisomers of the substituted cycloalkyl group at the 15-position of 6,19-ethano-ω-dihomo-6,9α-nitrolo-PGI₁ alkyl ester, nor any discussion of their possible activity.

As a result of research to identify compounds useful for the prevention or treatment of anoxia of brain cells it has now been found that the cis form of the compound 16,19-ethano-ω-dihomo-6,9α-nitrolo-PGI₁ alkyl ester has much superior activity in the trans form.

The present invention accordingly relates to a method for the prevention or treatment of anoxia of brain cells in a patient subject to or suffering therefrom which comprises the administration of an effective amount of a cis-16,19-ethanol-ω-dihomo-6,9α-nitrilo-PGI₁ alkyl ester (hereinafter referred to as the present compound), a cyclodextrin clathrate thereof, or a non-toxic salt thereof. Preferred salts of the present compound are organic acid salts such as the glucuronic acid salt. cis-16,19-Ethano-Ω-dihomo-6,9α-nitrilo-PGI₁ methyl ester, cyclodextrin clathrates and the glucuronic acid salt thereof are preferred.

The present invention also relates to the use in the preparation of a medicament for the treatment of anoxia of brain cells of a cis-16,19-ethano-Ω-dihomo-6,9α-nitrilo-PGI₁ alkyl ester of general formula I, or a cyclodextrin clathrate thereof, of a non-toxic salt thereof.

The method of the present invention may be employed in the treatment of brain anoxia caused by, for example, intracranial disease, as the present compounds possess a protective action against brain anoxia. Moreover, they do not cause side effects such as the suppression of breathing or circulatory insufficiency arising from inhibition over the entire central nervous system as their protective action on brain cell function is not caused by the inhibition of nerve action of the brain which results from the administration of hypnonarotic agents conventionally used for the treatment of anoxia of brain cells. Furthermore, hyponarcotic agents could be administered only at an acute stadium, whereas it is possible to carry out the method of the present invention at a chronic stadium and for the purpose of preventing relapse in view of the absence of the side effects associated with hypnonarcotic action. The prostaglandin analogues used in accordance with the present invention exhibit a protective action against anoxia of the brain at a low dose and have a potent action. In addition, their toxicity is low and accordingly their safety in use is high. For example, the compounds used in the present invention do not cause mortality when subcutaneously administered to mice at a dose of 30 mg/kg body weight which is more than 1000 times the minimum effective dose.

Accordingly the compounds used in the present invention can be used for the treatment of brain anoxia caused by intracranial diseases, and the various disturbances associated with such diseases. Furthermore, they can be used for the treatment of such diseases not only at an acute stadium but also at a subacute stadium and a chronic stadium, and for the purpose of preventing relapse.

The compounds used in the present invention are preferably administered parenterally (e.g. by intravenous, intraarterial, intramuscular, rectal or vaginal administration) or orally; parenteral administration is preferred.

Compositions for parenteral administration are known and include sterile aqueous or non-aqueous solutions, suspensions or emulsions, or sterile solid compositions which can be dissolved in sterile water or some other sterile injectable medium immediately before use.

Compositions for oral administration are known and include solid compositions such as tablets, pills, dispersible powders, capsules and granules, and liquid compositions such as emulsions, solutions, suspensions, syrups and elixirs.

The compounds may also be administered in other compositions which include suppositories for rectal administration or pessaries for vaginal administration.

The daily dosage to a human patient of the compounds used in the present invention is generally between 0.0001–100 mg/kg body weight, preferably between 0.0001–10 mg/kg body weight, more preferably between 0.0001–1 mg/kg body weight, by intravenous, intramuscular or subcutaneous administration or intravenous, intraarterial or subcutaneous infusion at the rate of 1–100 ng/kg/min during 1 hour to 24 hours and preferably between 0.0001–30 mg/kg body weight, more preferably between 0.0001–3 mg/kg body weight, by oral administration. However, the doses to be used are not limited to the ranges specified above because the doses depend on, for example, age, body, weight, the stage of diseases, the sort of disease of the patient, and times of administration.

The present invention is illustrated in more detail in the following Experimental Examples, Reference Examples and Preparative Examples.

The compounds used in the Experimental Examples are as follows:

| Sample | Name of Compound |
|---|---|
| T | cis-16,19-ethano-ω-dihomo-6,9α-nitrilo-PGI$_1$ methyl ester |
| V | trans-16,19-ethano-ω-dihomo-6,9α-nitrilo-PGI$_1$ methyl ester |

In the following tables * and ** show significance in the rate of danger below 5% and below 1% as compared with the control compounds.

EXPERIMENTAL EXAMPLE 1

PROLONGATION EFFECT ON TIME OF GASPING MOVEMENTS INDUCED BY COMPLETE ISCHEMIA IN MICE

The required amount of a sample was dissolved in 0.1 ml of ethanol, the solution was diluted with a 0.1M glycine-sodium hydroxide buffer solution (pH 10.0) and the solution was then subcutaneously and orally administered to one group comprising five Std-ddy male mice weighing 20–24 g, in a proportion of 0.1 ml per 10 g of the body weight of a mouse. At a maximum activity-exhibiting time (1.0 hour with Sample I by subcutaneous administration; 0.5 hour with Sample T by oral administration; 3.0 hours with Sample V by subcutaneous administration; 0.5 hour with Sample V by oral administration), the neck of the mouse was cut with scissors for decapitation and the time during which gasping movements, which appeared at the separated head, disappeared was measured. For comparison, a 0.1M glycine-sodium hydroxide buffer solution containing the same concentration of ethanol was likewise administered to the control group. Results are as shown in Table 1.

TABLE 1

| Route of administration | Sample | Dose (mg/kg) | Average Persistent Time (second ± standard error) |
|---|---|---|---|
| Subcutaneous administration | T | control | 20.4 ± 0.7 |
| | | 0.03 | 22.2 ± 0.4* |
| | | 0.1 | 22.8 ± 0.6* |
| | | 0.3 | 23.4 ± 0.5** |
| | | 1.0 | 26.4 ± 1.5** |
| | V | control | 19.2 ± 0.5 |
| | | 0.1 | 19.8 ± 0.6 |

TABLE 1-continued

| Route of administration | Sample | Dose (mg/kg) | Average Persistent Time (second ± standard error) |
|---|---|---|---|
| | | 1.0 | 20.2 ± 0.6 |
| | | 3.0 | 22.6 ± 1.1* |
| Oral administration | T | control | 20.0 ± 0.4 |
| | | 0.3 | 22.2 ± 0.5* |
| | | 1.0 | 23.0 ± 0.5** |
| | V | control | 20.0 ± 0.4 |
| | | 1.0 | 20.2 ± 0.4 |
| | | 3.0 | 22.2 ± 0.4* |

From the above results, Sample T of the present invention at the dose of 0.03 mg/kg body weight, and Sample V at the dose of 3.0 mg/kg body weight, exhibit a significant effect by subcutaneous administration on the time during which gasping movements persist following decapitation. Accordingly, the compound of the present invention (Sample T) is 100 times superior to the transisomer (Sample V). By oral administration, Sample T of the present invention exhibits a significant effect at the dose of 0.3 mg/kg body weight and Sample V at 3.0 mg/kg body weight. Accordingly, the compound of the present invention is 10 times superior to the transisomer.

EXPERIMENTAL EXAMPLE 2

EFFECT ON DEATH INDUCED BY POTASSIUM CYANIDE IN MICE

One group comprising five Std-ddy male mice weighing 20–24 g was prepared. The required amount of compound was dissolved in 0.1 ml of ethanol, the solution was diluted with a 0.1M glycine-sodium hydroxide buffer solution (pH 10.0), and was then subcutaneously and orally administered to the mice in a proportion of 0.1 ml per 10 g of the body weight of each mouse. At the maximum activity-exhibiting time (1.0 hour by subcutaneous and 0.5 hour by oral administration with Sample T; 3.0 hours by subcutaneous and 0.5 hour by oral administration with Sample V), a dose of 12.5 mg/kg body weight of potassium cyanide was administered intraperitoneally, and then the survival time until respiratory cessation of the mice was measured. For comparison, a 0.1M glycine-sodium hydroxide buffer solution containing the same concentration of ethanol was likewise administered to the control group. Results are as shown in Table 2.

TABLE 2

| Route of administration | Sample | Dose (mg/kg) | Average Survival Time (second ± standard error) |
|---|---|---|---|
| Subcutaneous administration | T | control | 146.0 ± 2.4 |
| | | 0.3 | 255.0 ± 19.3** |
| | | 1.0 | 322.0 ± 35.6** |
| | | 3.0 | 340.0 ± 61.3* |
| | V | control | 135.0 ± 7.1 |
| | | 0.3 | 135.0 ± 9.9 |
| | | 3.0 | 138.0 ± 6.6 |
| | | 10.0 | 176.0 ± 13.9* |
| Oral administration | T | control | 142.4 ± 10.0 |
| | | 0.3 | 174.0 ± 6.0* |
| | | 1.0 | 176.8 ± 2.9* |
| | V | control | 142.4 ± 10.0 |
| | | 1.0 | 144.8 ± 4.0 |
| | | 10.0 | 194.0 ± 5.6** |

From the above results, Sample T of the present invention at the dose of 0.3 mg/kg and Sample V at the dose of 10.0 mg/kg exhibit a significant effect by subcutaneous and oral administration in their action against brain anoxia associated with tissue poison induced by potassium cyanide. Accordingly the compound of the present invention (Sample T) is 30 times superior to the trans form (Sample V).

EXPERIMENTAL EXAMPLE 3

EFFECT ON CHANGE OF ENERGY METABOLITES IN THE BRAIN OF MICE EXPOSED BY HYPOXIC GAS MIXTURE

One group comprising five Std-ddy male mice weighing 20–24 g was prepared. The required amount of a compound was dissolved in 0.1 ml of ethanol, the solution was diluted with a 0.1M glycine-sodium hydroxide buffer solution (pH 10.0), and then subcutaneously and orally administered to the mice in a proportion of 0.1 ml per 10 g of the body weight of a mouse. After the Samples were administered at the time of maximum activity (1.0 hour by subcutaneous and 0.5 hour by oral administration with Sample T, and 3.0 hours by subcutaneous and 0.5 hour by oral administration with Sample V), and mice were put in a plastic-container of 2.5 liters volume, and a low oxygen content gaseous mixture consisting of 4% of oxygen and 96% of nitrogen was supplied at a rate of 4 liters per minute. After 240 seconds, the mice were thrown into liquid nitrogen and frozen. The content of energy metabolites in the brain was measured in accordance with the method of Lowry et al. (Journal of Biological Chemistry, Vol. 238, 18–30, 1964). The contents of creatine phosphate and adenosine triphosphate were measured as energy metabolites and the results are shown in Table 3.

A 0.1M glycine-sodium hydroxide buffer solution containing the same concentration of ethanol was administered to a control group. Results are also given for a group of mice not treated, which were not burdened by low oxygen and to which Sample I and Sample V were not administered.

TABLE 3

| Route of administration | Sample | Energy metabolites | Dose (mg/kg) | Average Content ($\mu$mol/g $\pm$ standard error) |
|---|---|---|---|---|
| Subcutaneous administration | T | creatine phosphate | not treated | 5.79 $\pm$ 0.15 |
| | | | control | 0.21 $\pm$ 0.05 |
| | | | 0.10 | 0.82 $\pm$ 0.32* |
| | | | 0.30 | 2.45 $\pm$ 0.52** |
| | | | 1.0 | 2.52 $\pm$ 0.64** |
| | | adenosine triphosphate | not treated | 3.20 $\pm$ 0.01 |
| | | | control | 0.82 $\pm$ 0.06 |
| | | | 0.03 | 1.44 $\pm$ 0.29* |
| | | | 0.10 | 1.69 $\pm$ 0.39** |
| | | | 0.30 | 2.85 $\pm$ 0.24** |
| | | | 1.0 | 2.82 $\pm$ 0.44** |
| | V | creatine phosphate | not treated | 4.61 $\pm$ 0.10 |
| | | | control | 1.42 $\pm$ 0.35 |
| | | | 1.0 | 2.09 $\pm$ 0.61 |
| | | | 3.0 | 3.65 $\pm$ 0.28** |
| | | adenosine triphosphate | not treated | 2.94 $\pm$ 0.06 |
| | | | control | 1.87 $\pm$ 0.30 |
| | | | 1.0 | 2.26 $\pm$ 0.38 |
| | | | 3.0 | 3.04 $\pm$ 0.04* |
| Oral administration | T | creatine phosphate | not treated | 5.79 $\pm$ 0.15 |
| | | | control | 0.21 $\pm$ 0.05 |
| | | | 0.3 | 1.60 $\pm$ 0.54** |
| | | | 3.0 | 3.00 $\pm$ 0.84** |
| | | adenosine triphosphate | not treated | 3.20 $\pm$ 0.01 |
| | | | control | 0.82 $\pm$ 0.06 |
| | | | 0.3 | 2.09 $\pm$ 0.45** |
| | | | 3.0 | 2.40 $\pm$ 0.37** |
| | V | creatine phosphate | not treated | 4.61 $\pm$ 0.10 |
| | | | control | 1.42 $\pm$ 0.35 |
| | | | 3.0 | 1.20 $\pm$ 0.30 |
| | | | 10.0 | 1.77 $\pm$ 0.35 |
| | | adenosine triphosphate | not treated | 2.94 $\pm$ 0.06 |
| | | | control | 1.87 $\pm$ 0.30 |
| | | | 3.0 | 2.06 $\pm$ 0.39 |
| | | | 10.0 | 2.76 $\pm$ 0.08* |

From above results, the difference between the compound of the present invention and the trans-form is described below in terms of the effect on energy metabolites in the brain of the mice burdened by low oxygen. By subcutaneous administration Sample T of the present invention exhibits a significant effect on creatine phosphate levels at a dose of 0.10 mg/kg body weight and Sample V of the trans form at a dose of 3.0 mg/kg body weight and therefore Sample T of the present invention is 30 times superior to Sample V of the trans form: by oral administration, Sample T of the present invention exhibits a significant effect at a dose of 0.3 mg/kg body weight and Sample V of the trans form does not exhibit a significant effect even at a dose of 10.0 mg/kg and therefore Sample T is more than 30 times superior to Sample V. By subcutaneous administration Sample T of the present invention exhibits a significant effect on adenosine triphosphate levels at a dose of 0.03 mg/kg body weight and Sample V at a dose of 3.0 mg/kg body weight, and therefore Sample T in the present invention is 100 times superior to Sample V of the trans form: by oral administration Sample T of the present invention exhibits a significant effect at a dose of 0.3 mg/kg body weight and Sample V at a dose of 10.0 mg/kg body weight, and therefore Sample T is 30 times superior to Sample V.

As the results from Experimental Examples 1 to 3 demonstrate, the compound of the present invention exhibits from 10 to 100 times stronger an effect than the trans form in its protective activity against brain anoxia.

Cis-16,19-ethano-$\omega$-dihomo-6,9$\alpha$-nitrilo-PGI$_1$ methyl ester of the present invention may be synthesized by, for example, the following scheme, in which THP represents the tetrahydropyran-2-yl group, Ac represents the acetyl group and Ts represents the tosyl group.

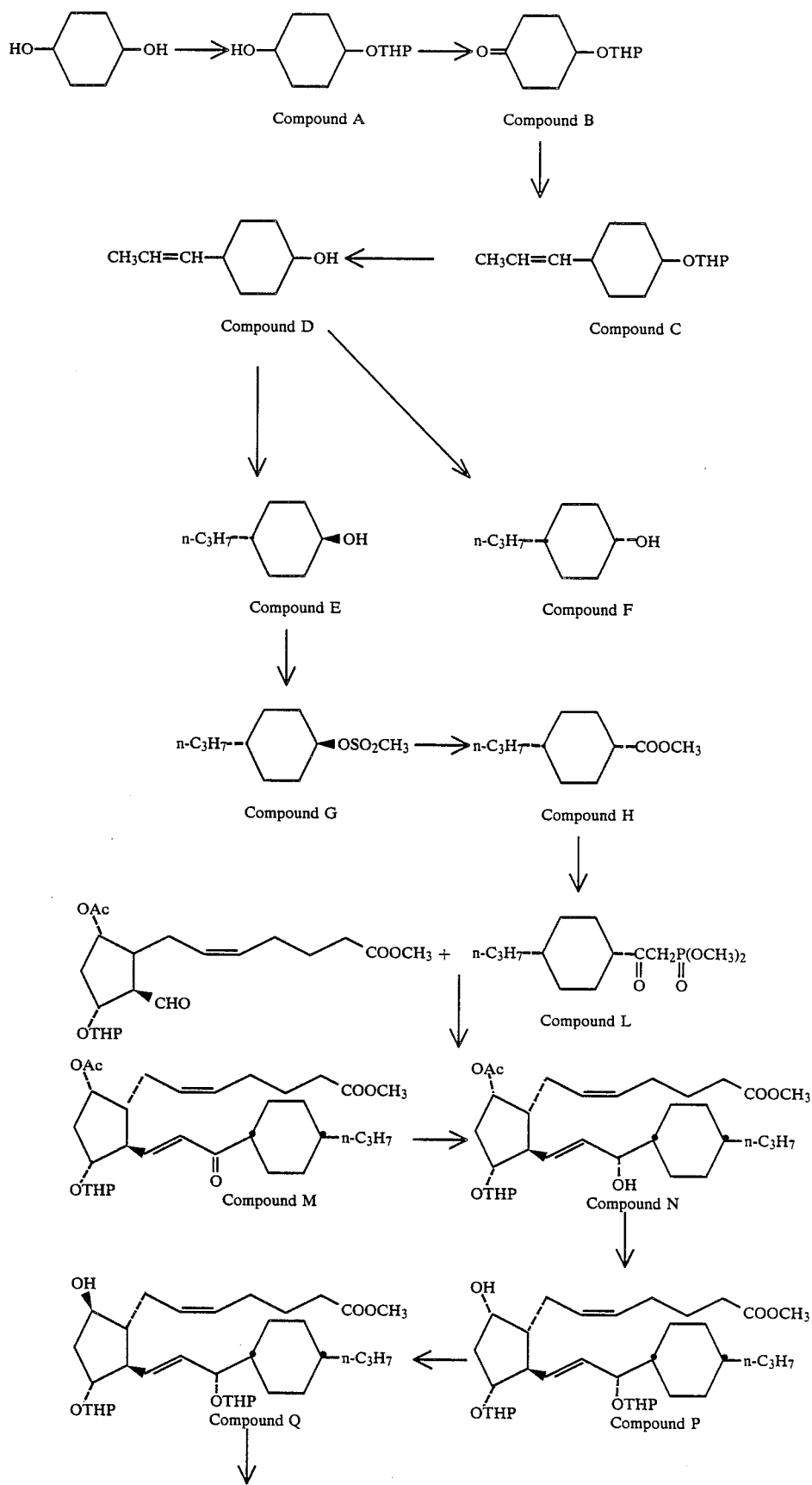

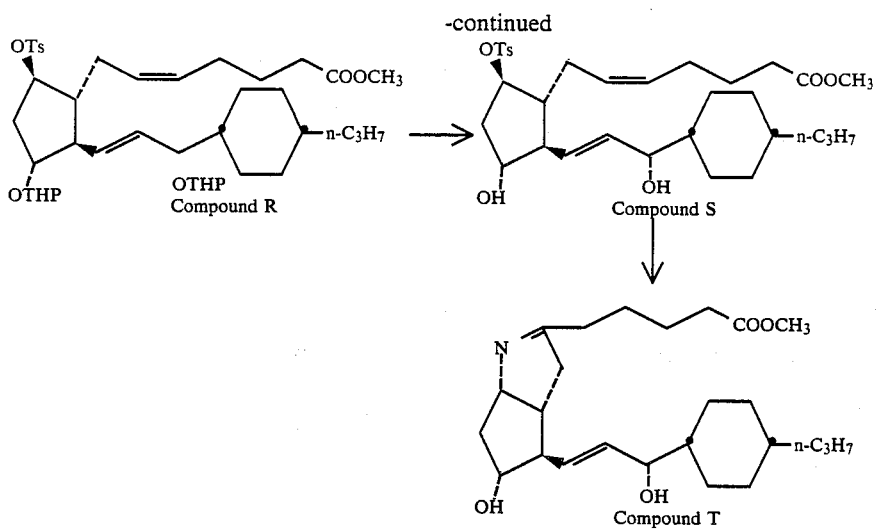

The following Reference Examples illustrate suitable methods for carrying out each of the steps indicated in the scheme shown above.

Except when specified otherwise, infrared absorption spectra were recorded by the liquid film method and nuclear magnetic resonance spectra were recorded in deuterochloroform solution.

REFERENCE EXAMPLE 1

Synthesis of

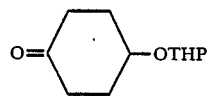
(Compound L)

(1) Synthesis of

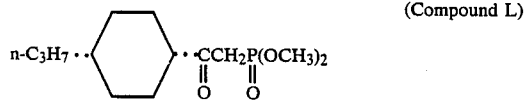
(Compound A)

A suspension of 30 g of 1,4-cyclohexanediol (mixture of trans form and cis form) in 2.5 liters of methylene chloride was stirred at 0° C. A catalytic amount of p-toluenesulfonic acid was added thereto and then a solution of 21.7 g of 2,3-dihydropyran in 100 ml of methylene chloride was added thereto over 30 minutes. The mixture was stirred for 15 minutes at 0° C. and then for 30 minutes at room temperature. After addition of 10 drops of triethylamine thereto, the mixture was further stirred for two to three minutes. The reaction mixture was concentrated under reduced pressure and the obtained residue was purified by column chromatography on silica gel (n-hexane:ethylacetate=2:1→1:1) to give 28 g of Compound A having the following physical data:

NMR: δ 4.75(1H, m), 4.00–3.83(1H, m), 3.83–3.66(2H, m), 3.57–3.42(1H, m).

(2) Synthesis of

(Compound B)

Under an atmosphere of argon, a solution of 46.6 ml of dimethyl sulfoxide in 100 ml of methylene chloride was slowly added dropwise to a solution of 24.4 ml of oxalyl chloride in 2.5 liters of methylene chloride at −78° C. and the mixture was stirred for 20 minutes at the same temperature. To the obtained solution was added dropwise a solution of 28 g of Compound A in 70 ml of methylene chloride at a temperature not more than −60° C. and the mixture was stirred for one hour at −78° C. After slowly adding 105 ml of triethylamine, the reaction mixture was stirred for 20 minutes at −78° C. and then allowed to warm to room temperature by removal of refrigerant. In the course of warming, the reaction mixture was vigorously stirred for 30 minutes after addition of 400 ml of water at a temperature in the vicinity of 0° C. The organic layer of the reaction mixture was concentrated under reduced pressure and the aqueous layer thereof was extracted with diethyl ether. The extract and the residue previously obtained by concentrating were combined and the mixture was washed with water and a saturated aqueous solution of sodium chloride, successively, dried over anhydrous magnesium sulfate and concentrated under reduced pressure. The residue was purified by column chromatography on silica gel (n-hexane:ethyl acetate=4:1→1:1) to give 27.4 g of Compound B having the following physical data.

NMR: δ 4.76(1H, q), 4.15–4.03(1H, m), 4.00–3.85(1H, m), 3.63–3.45(1H, m).

MS: m/e 198(M+).

(3) Synthesis of

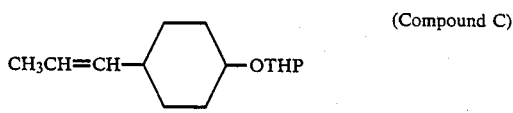
(Compound C)

Under an atmosphere of argon, 115 ml of a 1.5M solution of n-butyllithium in n-hexane was added slowly to a solution of 66.6 g of propyltriphenylphosphonium bromide in 500 ml of dry tetrahydrofuran at 0° C. and the mixture was stirred for seven minutes at the same temperature. To the obtained solution was slowly added dropwise a solution of 27.4 g of Compound B in 50 ml of tetrahydrofuran and the mixture was stirred for 30 minutes at the same temperature and then for 30 minutes at room temperature. After addition of 50 ml of water and reaction mixture was concentrated under reduced pressure. The residue was purified by column chromatography on silica gel (methylene chloride:n-hexane=2:1) to give 24.65 g of Compound C having the following physical data.

NMR: δ 5.10(1H, t), 4.80–4.64(1H, m), 4.10–3.62(2H, m), 3.62–3.30(1H, m), 0.90(3H, t).

MS: m/e 224(M+), 139, 122.

(4) Synthesis of

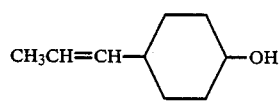
(Compound D)

A mixture of 24.6 g of Compound C, 0.5 g of p-toluenesulfonic acid monohydrate and 250 ml of methanol was stirred for one hour at room temperature. After addition of several drops of triethylamine thereto, the reaction mixture was concentrated under reduced pressure. The residue was distilled to give 13.9 g of Compound D having the following physical data.

bp: 78° C./4 mmHg.

NMR: δ 5.12(1H, t), 8.98–8.62(1H, m), 0.92(3H, t).

MS: m/e 140(M+), 122.

(5) Synthesis of

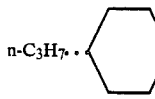 and 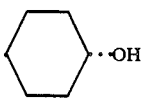

(Compound E)    Compound F
                (the corresponding
                cis form)

To a solution of 13.9 g of Compound D in 140 ml of methanol was added 1.4 g of palladium on carbon (content: 5%) and the mixture was stirred for 14 hours at room temperature under an atmosphere of hydrogen. The reaction mixture was filtered through a layer of celite and the filtrate was concentrated under reduced pressure. The residue was purified by column chromatography on silica gel (n-hexane: ethyl acetate=4:1) to give 8.42 g of the mixture of Compound E and F.

8.4 g of the mixture of cis form and trans form was purified by chromatography on a Lobar ® column ("Lobar" is a registered Trade Mark of Merck & Co., Inc.) (n-hexane: ethyl acetate=9:1→8.5:1.5) to give 5.55 g of Compound E and 1.96 g of Compound F having the following physical data:

(a) Compound E (trans form)

NMR: δ 3.64–3.45(1H, tt), 2.04–1.88(2H, m), 1.83–1.65(2H, m), 1.57(1H, br), 1.03–0.86(5H, m+t).

MS: m/e 142(M+), 124.

(b) Compound F (cis form)

NMR: δ 4.00–3.89(1H, m), 0.89(3H, t).

MS: m/e 142(M+), 124.

(6) Synthesis of

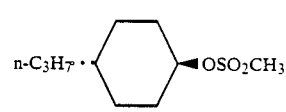
(Compound G)

Under an atmopshere of argon, a solution of 5.45 g of Compound E in 50 ml of methylene chloride was allowed to cool to −20° C. and thereto were added 8.50 µl of triethylamine and then 4.44 ml of mesyl chloride. The mixture was stirred for 20 minutes at the same temperature. The reaction mixture was diluted with 200 ml of ethyl acetate, and washed with a saturated aqueous solution of sodium bicarbonate and a saturated aqueous solution of sodium chloride, successively, dried over anhydrous magnesium sulfate and concentrated under reduced pressure. The residue was purified by column chromatography on silica gel (n-hexane: ethyl acetate=4:1) to give 8.78 g of Compound g having the following physical data.

NMR: δ 4.58(1H, tt), 3.00(3H, s), 2.20–2.05(2H, m), 0.88(3H, t).

MS: m/e 124.

(7) Synthesis of

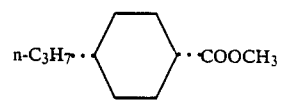
(Compound H)

Under an atmosphere of argon, 5.34 g of sodium cyanide was dissolved in 40 ml of dimethyl sulfoxide with heating, and to the solution thus obtained was added a solution of 8.00 g of Compound G in 10 ml of dimethyl sulfoxide at 70° C. to 80° C., and then the mixture,was stirred for four hours at 100° C. After cooling to room temperature, the reaction mixture was poured into 250 ml of ice-water and extracted with a mixture of diethyl ether and n-pentane (1:1). The extract was washed with water and a saturated aqueous solution of sodium chloride, successively, and concentrated at atmospheric pressure to give 5.17 g of cis-4-propylcyclohexanecarbonitrile (Compound J) as crude product having the following physical data:

IR (chloroform solution): ν 2225 cm$^{-1}$.

To 5.17 g of Compound J was added 30 ml of a mixture of water and conc. sulfuric acid (1:1) and the mixture was stirred for three hours at 110° C. to 130° C. After cooling to room temperature, the reaction mixture was poured into 60 ml of water and extracted with ethyl acetate, and then the extract was concentrated under reduced pressure. To the residue was added 30 ml of 1N aqueous solution of sodium hydroxide and the mixture was stirred for five minutes at room temperature. The alkaline aqueous solution was extracted with diethyl ether to remove the neutral substance, and the remaining aqueous solution was adjusted again to pH 3 with 3N hydrochloric acid and extracted with ethyl acetate. The extract was washed with water and a saturated aqueous solution of sodium chloride, successively, dried over anhydrous magnesium sulfate and concentrated under reduced pressure to give 1.91 g of cis-4-propylcyclohexanecarboxylic acid (Compound K) as crude product having the following physical data:

NMR: δ 7.00–5.00(1H, br), 2.56(1H, m), 0.88(3H, t).

IR (chloroform solution): ν −2650, 1690 cm$^{-1}$.

1.91 g of Compound K was dissolved in 20 ml of diethyl ether and allowed to cool to 0° C. To the solution was added dropwise an ethereal solution of diazomethane until the reaction mixture turned to pale yellow and then the reaction mixture was concentrated under reduced pressure. The residue was purified by column chromatography on silica gel (n-hexane: ethyl acetate=9:1) to give 1.73 g of Compound H having the following physical data.

NMR: 3.67(3H, s), 2.65–2.40(1H, m), 0.87(3H, t).
IR (chloroform solution): $\nu$ 1720 cm$^{-1}$.
MS: m/e 184(M+), 153, 152.

(8) Synthesis of

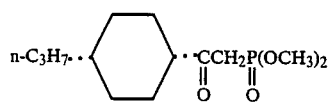
(Compound L)

A solution of 1.347 g of dimethyl methylphosphonate in 30 ml of dry tetrahydrofuran was allowed to cool to −78° C. To the solution was added dropwise slowly 7.44 ml of a 1.45 solution of n-butyllithium in n-hexane at a temperature not more than −60° C. and the mixture was stirred for 15 minutes at the same temperature. To the mixture thus obtained was added dropwise slowly a solution of 1.00 g of Compound H in two ml of dry tetrahydrofuran at a temperature not more than −60° C., and the mixture was stirred for 2.5 hours at −78° C. and adjusted to pH 3 to 4 with acetic acid and then allowed to warm to room temperature. The reaction mixture was diluted with 200 ml of ethyl acetate, washed with a small amount of water, dried over anhydrous magnesium sulfate and concentrated under reduced pressure. The residue was purified by column chromatography on silica gel (ethyl acetate) to give 1.25 g of Compound L having the following physical data:

NMR: δ 3.77(6H, d), 3.13(2H, d), 2.75–2.62(1H, m), 0.86(3H, t).
MS: m/e 276(M+), 151, 123.

REFERENCE EXAMPLE 2

Snythesis of

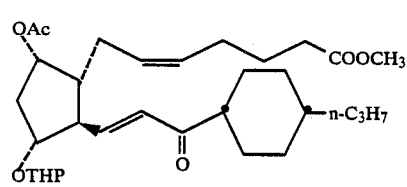
(Compound M)

To a suspension of 0.152 g of sodium hyride (content: 64%) in 10 ml of dry tetrahydrofuran was added dropwise slowly a solution of 1.25 g of Compound L in 5 ml of dry tetrahydrofuran under cooling with water and the mixture was stirred for 15 minutes at room temperature. Thereto was added all at once a solution of 1.55 g of 1α-acetoxy-2α-(6-methoxycarbonylhex-cis-2-enyl)-3β-formyl-4α-(tetrahydropyran-2-yloxy)cyclopentane (prepared as described in the specification of the British Patent No. 1482928) in 6 ml of dry tetrahydrofuran at room temperature and the mixture was stirred for one hour at room temperature. The reaction mixture was adjusted to pH 3 by adding acetic acid, and then filtered through a layer of celite. The filtrate was concentrated under reduced pressure (acetic acid was removed by concentrating under reduced pressure with addition of toluene). The residue was purified by column chromatography on silica gel (n-hexane: ethyl acetate=4:1) to give 1.79 g of Compound M having the following physical data.

NMR: δ 6.83–6.66(1H, dd×2), 6.40–6.29(1H, d×2), 5.45–5.22(2H, m), 5.15–5.04(1H, m), 4.61–4.48(1H, m), 4.17–3.91(1H, m), 3.67(3H, s), 3.91–3.67(3H, m), 3.53–3.32(2H, m), 2.29(2H, t,), 1.05–0.91(3H, t).
IR (chloroform solution): $\nu$ 2910, 2850, 1720, 1680, 1650, 1610, 1430, 1370, 1240, 1010, 960 cm$^{-1}$.
MS: m/e 546(M$^{30}$), 515, 462.

REFERENCE EXAMPLE 3

Snythesis of

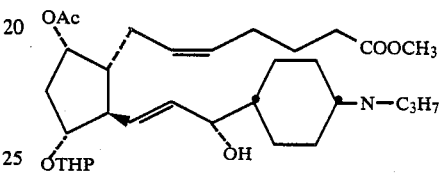
(Compound N)

Under an atmosphere of argon, to a suspension of 0.915 g of lithium aluminium hydride in 44 ml of dry tetrahydrofuran were added dropwise slowly a mixture of 1.13 ml of ethanol and 8 ml of dry tetrahydrofuran at 5° C. and then added dropwise slowly a solution of 5.57 g of S-2,2'-dihydroxy-1,1'-binaphthyl (SBN) in 20 ml of dry tetrahydrofuran. The mixture thus obtained was stirred for 15 minutes at room temperature, and then allowed to cool to −78° C. Thereto was added dropwise slowly a solution of 1.78 g of Compound M in 9 ml of dry tetrahydrofuran and the mixture was stirred for 15 minutes at the same temperature. After adding carefully 20 ml of methanol to reaction mixture at −78° C., it was allowed to warm gradually. At −40° C., the reaction mixture was adjusted to pH 3 to 4 by adding 3N hydrochloric acid and then allowed to warm to room temperature. The reaction mixture thus obtained was diluted with ethyl acetate in five-fold volume the reaction mixture, and the precipitated solid was filtered off. The filtrate was washed with a saturated aqueous solution of sodium bicarbonate and a saturated aqueous solution of sodium chloride, successively, dried over anhydrous magnesium sulfate and concentrated under reduced pressure. A large quantity of solid SBN precipitated in the course of concentration was ground enough with benzene and filtered off, and then the filtrate was again concentrated under reduced pressure. The obtained residue was purified by column chromatography on silica gel (methylene chloride→methylene chloride: ethyl acetate=4:1) to give 868 mg of Compound N having the following physical data and 132 mg of the corresponding 15β-hydroxy compound.

NMR: δ 5.75–5.43(2H, m), 5.43–5.25(2H, m), 5.13–5.00(1H, m), 4.73–4.55(1H, m), 4.06–3.75(3H, m), 3.68(3H, s), 3.53–3.34(1H, m), 2.05(3H, s).
IR (chloroform solution): $\nu$ 3500, 2900, 2850, 1720 cm$^{-1}$.
MS: m/e 464, 446.

REFERENCE EXAMPLE 4

Synthesis of (Compound P)

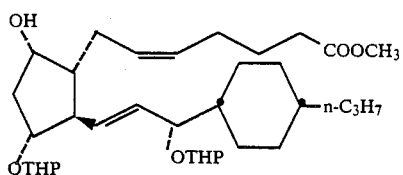

A mixture of 0.868 g of Compound N, 0.149 ml of 2,3-dihydropyran, 5 ml of methylene chloride and 2 mg of p-toluenesulfonic acid was stirred for 10 minutes at room temperature. After adding several drops of triethylamine, the reaction mixture was concentrated under reduced pressure to give the 15-(tetrahydropyran-2-yloxy) compound. The obtained residue (the 15-(tetrahydropyran-2-yloxy) compound) was dissolved in 5 ml of methanol and thereto was added 0.204 g of potassium carbonate and the mixture was stirred for one hour at 40° C. to 50° C. The reaction mixture was diluted with 50 ml of diethyl ether, washed with water and a saturated aqueous solution of sodium chloride, successively, dried over anhydrous magnesium sulfate and concentrated under reduced pressure. The residue was purified by column chromatography on silica gel (methylene chloride: ethyl acetate=9:1) to give 620 mg of Compound P having the following physical data.

NMR: δ 5.60–5.18(4H, m), 4.80–4.62(2H, brx2), 4.18–3.71(5H, m), 3.67(3H, s), 3.58–3.30(2H, m), 0.88(3H, t).

IR: ν 3450, 1710 cm⁻¹.

MS: m/e 488, 404.

REFERENCE EXAMPLE 5

Synthesis of (Compound Q)

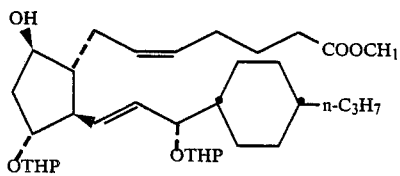

To a mixture of 0.620 g of Compound P, 0.550 g of triphenylphosphine, 79 μl of formic acid and 5 ml of dry tetrahydrofuran, was added slowly a solution of 0.330 ml of diethylazodiformate in one ml of dry tetrahydrofuran at a temperature in the vicinity of 5° C., and the mixture was stirred for one hour at the same temperature. The reaction mixture was poured into 50 ml of a saturated aqueous solution of sodium bicarbonate and extracted with ethyl acetate. The extract was washed with water and a saturated aqueous solution of sodium chloride, successively, dried over anhydrous magnesium sulfate and concentrated under reduced pressure. The residue was purified by column chromatography on silica gel (n-hexane: ethyl acetate=7:1) to give 600 mg of the 11β-formyloxy compound.

To a solution of 600 mg of the obtained formyloxy compound in 4 ml of methanol was added 0.145 g of potassium carbonate and the mixture was stirred for 15 minutes at room temperature. The reaction mixture was diluted with 40 ml of ethyl acetate, washed with water and a saturated aqueous solution of sodium chloride, successively, dried over anhydrous magnesium sulfate and concentrated under reduced pressure. The residue was purified by column chromatography on silica gel (n-hexane: ethyl acetate=4:1) to give 441 mg of Compound Q having the following physical data.

NMR: δ 5.67–5.19(4H, m), 4.82–4.59(2H, brx2), 4.19–3.76(5H, m), 3.68(3H, s), 3.62–3.38(2H, m), 0.89(3H, t).

MS: m/e 488, 457.

REFERENCE EXAMPLE 6

Synthesis of (Compound R)

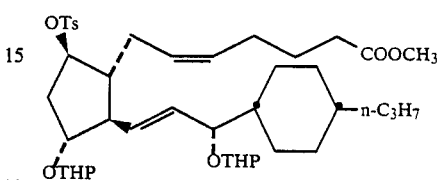

A mixture of 0.44 g of Compound Q, 427 mg of tosyl chloride and 7 ml of dry pyridine was stirred for 20 hours at room temperature. The reaction mixture was diluted with 100 ml of ethyl acetate, washed with 1N hydrochloric acid, a saturated aqueous solution of sodium bicarbonate and a saturated aqueous solution of sodium chloride, successively, dried over anhydrous magnesium sulfate and concentrated under reduced pressure. The residue was purified by column chromatography on silica gel (n-hexane: ethyl acetate=9:1→4:1) to give 460 mg of Compound R having the following physical data.

NMR: δ 7.78(2H, d), 7.32(2H, d), 5.60–5.10(4H, m) 4.75–4.50(3H, m), 4.13–3.60(7H, m+s), 3.55–3.31(2H, m), 2.44(3H, s), 1.00–0.80(5H, m+t).

REFERENCE EXAMPLE 7

Synthesis of (Compound S)

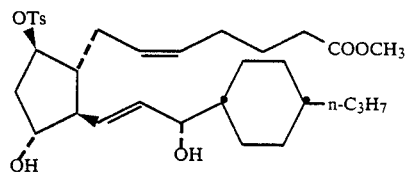

A mixture of 0.460 g of Compound R, 10 mg of p-toluenesulfonic acid monohydrate and 5 ml of methanol was stirred for one hour at room temperature. After adding thereto several drops of triethylamine, the reaction mixture was concentrated under reduced pressure. The residue was purified by column chromatography on silica gel (n-hexane: ethyl acetate=1:1→1:2) to give 330 mg of Compound S having the following physical data.

NMR: δ 7.75(2H, d), 7.32(2H, d), 5.44(2H, m), 5.23(2H, m), 4.05–3.86(2H, m), 3.66(3H, s), 2.45(3H, s), 2.28(2H, t), 0.88(3H, t).

IR: ν 3400, 3080, 3060, 3020, 1950, 1850, 1745, 1590, 1480, 1440, 1350, 1230, 1180, 1090, 975 cm⁻¹.

MS: m/e 404, 386.

REFERENCE EXAMPLE 8

Synthesis of

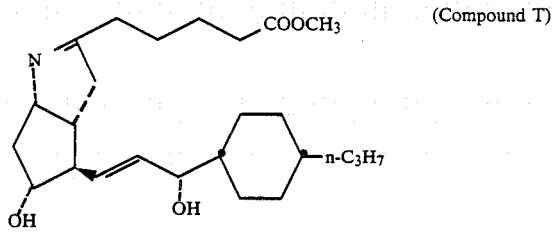

(Compound T)

A mixture of 0.165 g of Compound S, 37 mg of sodium azide and 20 ml of dry dimethyl sulfoxide was stirred for 19 hours at a temperature in the vicinity of 40° C. The reaction mixture was poured into 20 ml of ice-water and extracted with a mixture of ethyl acetate and diethyl ether (1:1). The extract was washed with a saturated aqueous solution of sodium chloride, dried over anhydrous magnesium sulfate and concentrated under reduced pressure to give 161 mg of the 9α-azido compound.

A solution of 161 mg of the obtained 9α-azido compound in 3 ml of dry toluene was stirred for 20 hours at a temperature in the vicinity of 70° C. and the reaction mixture was allowed to cool to room temperature. The reaction mixture was concentrated under reduced pressure and the residue was purified by column chromatography on silica gel (ethyl acetate→ethyl acetate:methanol=95:5) to give 87 mg of Compound T having the following physical data.

NMR: δ 5.64–5.42(2H, m), 4.47–4.32(1 H, m), 4.05–3.77(2H, mx2), 3.67(3H, s), 0.90(3H, t).

IR: ν 3350, 2900, 2850, 1730, 1630, 1430, 1370, 1230, 970 cm$^{-1}$.

MS: m/e 419(M+), 401, 388.

HPLC: retention time: 6.09 min;
  column: TSK-gel (LS-410) ® (it is a registered Trade Mark of Toyo Jozo KK);
  flow rate: 0.5 ml/min;
  temperature: room temperature;
  sample size: 10 μg injection (0.5 mg/ml);
  mobile phase: 0.02% KH$_2$PO$_4$ in acetonitrile.

REFERENCE EXAMPLE 9

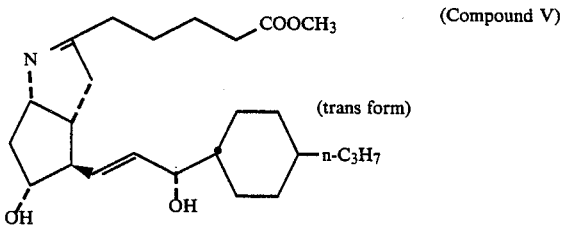

(Compound V)
(trans form)

(1) Synthesis of

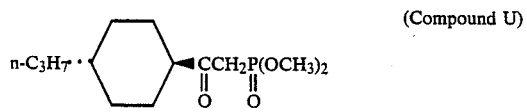

(Compound U)

By the same procedures as described in Reference Example 1-(6) to 1-(8), Compound U having the following physical data was obtained by using Compound F prepared in Reference Example 1-(5) as a starting material.

NMR: δ 3.77(6H, d), 3.13(2H, d), 2.50(1H, tt), 0.87(3H, t).

MS: m/e 276(M+), 151, 123.

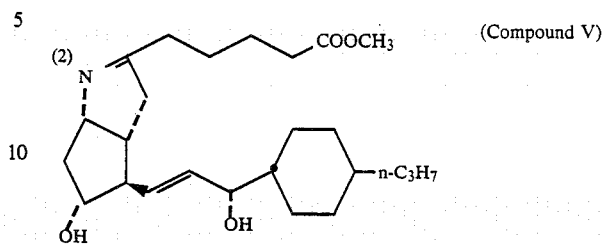

(Compound V)
(2)

By the same procedures as described in Reference Examples 2 to 8, Compound V having the following physical data was obtained by using Compound U and 1α-acetoxy-2α-(6-methoxycarbonylhex-cis-2-enyl)-3β-formyl-4α-(tetrahydropyran-2-yloxy)cyclopentane.

NMR: δ 5.64–5.42(2H, m), 4.47–4.32(1H, m), 3.92–3.75(2H, m) 3.67(3H, s), 1.05–0.90(6H, m+t).

IR: ν 3350, 2900, 2850, 1730, 1630, 1430, 1370, 1230, 970 cm$^{-1}$.

MS: m/e 419(M$^{30}$), 401, 388.

HPLC: retention time: 7.39 min;
  column: TSK-gel (LS-410) ®; (it is a registered Trade Mark of Toyo Jozo KK);
  flow rate: 0.5 ml/min;
  temperature: room temperature;
  sample size: 10 μg injection (0.5 mg/ml);
  mobile phase: 0.02% KH$_2$PO$_4$ in acetonitrile.

REFERENCE EXAMPLE 10

Synthesis of D-glucuronic acid salt of Compound T

To a solution of 50 mg of Compound T in 5 ml of ethanol, was added a solution of 25.5 mg of D-glucuronic acid in 5 ml of water at room temperature and the mixture was stirred enough. The reaction mixture was concentrated under reduced pressure and dried in vacuo to give 72 mg of the title compound as white powder, having the following physical data.

NMR (methanol-d$_4$ solution): δ 5.65–5.4(2H, m), 5.18(1H, d), 4.52(1H, d), 4.25(1H, d), 3.96–3.8(1H, m), 3.72(1H, dt), 3.68(3H, s), 3.6–3.4(2H, m), 2.78–2.30(3H, m), 2.10–2.0(1H, m), 1.75–1.10(18H, m), 0.90(3H, t).

IR (KBr method): ν 3350, 2900, 1725, 1670, 1590, 1420, 1400, 1080, 1040 cm$^{-1}$.

PREPARATIVE EXAMPLE 1

50 mg of cis-16,19-ethano-ω-dihomo-6,9α-nitrilo-PGI$_1$ methyl ester (compound T) was dissolved in 10 ml of ethanol. The solution was mixed with 18.5 g of mannitol. After passing the mixture through a 30 mesh sieve and drying at 30° C. for 90 minutes, the mixture was again passed through a 30 mesh sieve.

To the powder obtained 200 mg of Aerosil (microfine silica) was added and the mixture was filled into 100 No. 3 hard gelatin capsules to obtain gastric capsules containing 0.5 mg of cis-16,19-ethano-ω-dihomo-6,9α-nitrilo-PGI$_1$ methyl ester (compound T) per capsule.

PREPARATIVE EXAMPLE 2

0.5 mg of cis-16,19-ethano-ω-dihomo-6,9α-nitrilo-PGI$_1$ methyl ester (compound T) was dissolved in 5 ml of ethanol and the solution was sterilized by filtration through a bacteria-retaining filter. The solution was placed in 0.1 ml portions in 1 ml ampoules to obtain ampoules each containing 10 μg of cis-16,19-ethano-ω-dihomo-6,9α-nitrilo-PGI$_1$ methyl ester (compound T): the ampoules were then sealed. The content of each ampoule after dilution to an appropriate volume, e.g., by diluting with a tris-hydrochloric acid buffer solution (pH 8.6) to 1 ml, is suitable for use as an injectable solution.

PREPARATIVE EXAMPLE 3

To a solution of 50 mg of cis-16,19-ethano-ω-dihomo-6,9α-nitrilo-PGI$_1$ methyl ester (compound T) and 1.6 g of α-cyclodextrin in 10 ml of distilled water, 10 mg of citric acid, 50 g of lactose and 800 ml of distilled water were added to obtain a solution and distilled water was added thereto to make the total volume 1 liter. Thereafter, sterile filtration was performed in a conventional manner and the solution was placed, in 1 ml portions, in ampoules. After freeze drying, the ampoules were sealed to obtain a freeze dried preparation suitable for use, after dissolution, as an injectable solution.

I claim:

1. A method for the prevention or treatment of anoxia of brain cells in a patient subject to or suffering therefrom which comprises the administration of an amount effective to prevent or treat said anoxia of a cis-16,19-ethano-ω-dihomo-6,9α-nitrilo-PGI$_1$ alkyl ester of the general formula:

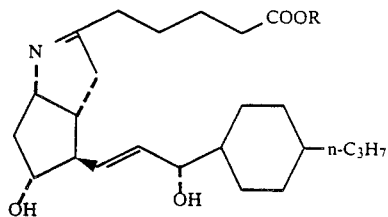

(wherein R represents an alkyl group of from 1 to 4 carbon atoms in a straight or branched chain) or a cyclodextrin clathrate thereof, or a non-toxic salt thereof.

2. A method according to claim 1 in which R represents a methyl group.

3. A pharmaceutical composition useful for the prevention or treatment of anoxia of brain cells which comprises an amount effective to prevent or treat said anoxia of a cis-16,19-ethano-ω-dihomo-6,9α-nitrilo-PGI$_1$ alkyl ester as defined in claim 1 or a cyclodextrin clathrate thereof, or a non-toxic salt thereof, in association with a pharmaceutically acceptable diluent or carrier.

4. A pharmaceutical composition according to claim 3 wherein the alkyl ester is the methyl ester.

* * * * *